United States Patent [19]

Klauschenz et al.

[11] Patent Number: 5,162,533

[45] Date of Patent: Nov. 10, 1992

[54] 3-CYANO-5,4'-BIPYRIDINE-1'-OXIDE COMPOUNDS AND PHARMACEUTICAL COMPOSITIONS AND METHODS CONTAINING THE SAME

[75] Inventors: Erhard Klauschenz; Volker Hagen; Angela Hagen; Peter Muschick; Brigitte Schlegel, all of Berlin; Sabine Heer, Dresden; Gottfried Faust; Hans-Joachim Jänsch, both of Radebeul, all of Fed. Rep. of Germany

[73] Assignee: Arzneimittelwerk Dresden G.m.b.H., Radebeul, Fed. Rep. of Germany

[21] Appl. No.: 665,682

[22] Filed: Mar. 7, 1991

[30] Foreign Application Priority Data

Mar. 9, 1990 [DD] German Democratic Rep. ... 338543

[51] Int. Cl.⁵ .................. A61K 31/44; A61K 31/495; A61K 31/535; C07D 249/16
[52] U.S. Cl. .................................. 546/257; 544/124; 544/360; 546/258
[58] Field of Search ............... 546/257, 258; 544/124, 544/360; 514/237.2, 255, 334

[56] References Cited

U.S. PATENT DOCUMENTS 4,264,603  4/1981  Lesher et al. .................. 546/257
4,362,734 12/1982  Lesher et al. .................. 546/257
4,463,008  7/1984  Lesher et al. .................. 546/257

OTHER PUBLICATIONS

Chemical Abstracts, vol. 79, No. 25, Abstract No. 145840q, p. 272, Dec. 24, 1973, Kireev et al.

Primary Examiner—Dale R. Ore
Attorney, Agent, or Firm—Schweitzer Cornman & Gross

[57] ABSTRACT

A 3-cyano-5,4'-bipyridine-1'-oxide of the formula

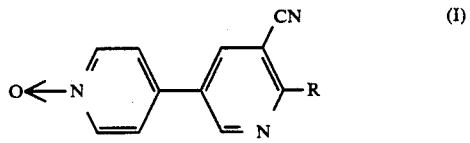

and their pharmaceutically acceptable acid addition salts, wherein R is an amino, alkoxy, oxyalkoxy or chloro residue, have heart stimulating cardiotonic and vasodiolatory properties. They can be preparaed by (a) converting an R-substituted-3-cyano-bipyridine to its corresponding N-oxide, or (b) by substituting an R-residue or an R-unsubstituted precursor of the conpound of fomula (i), and if required, converting the product into its pharmaceutically acceptable acid addition salt.

6 Claims, No Drawings

3-CYANO-5,4'-BIPYRIDINE-1'-OXIDE COMPOUNDS AND PHARMACEUTICAL COMPOSITIONS AND METHODS CONTAINING THE SAME

FIELD OF THE INVENTION

The present invention relates to 3-cyano-5,4'-bipyridine-1'-oxide, a process for making, and its use as a heart stimulant, cardiotonic, and vasodilator.

BACKGROUND OF THE INVENTION

2-Amino- and 2-alkylamino-3-cyano-5-pyridyl-pyridines are known e.g. from U.S. Pat. No. 4,362,734, East German patent Nos. 263,758; and 275,047, and from an article in, Die Pharmazie 44, 20, (1989). 2-aminoalkylamino-3-cyano-, 3-cyano-2-oxyaxlkoxy-, and 3-cyano-2-oxyalkylamino-5-(pyrid-4-yl)-pyridines, and 3-cyano-2-morpholino-5-(pyrid-4-yl)-pyridine and their cardiotonic action are described in European patent No. 200,024 A2.

Likewise, 2-chloro-3-cyano-, and 2-alkoxy-3-cyano-5-(pyrid-4-yl)-pyridines and the cardiotonic activity of the latter compound are described, for example, in, Pol. J. Pharmacol. 30, 707 (1978), and also in U.S. Pat. Nos. 4,264,603; 4,463,008; and Spanish patent No. 518,498).

Biologically active heterocyclic compounds are frequently also administered in the form of their pharmaceutically acceptable acid addition salts, such as in the form of their hydrochlorides, sulfates, acetates, fumarates, mesylates or tartrates, as described in German published patent application No. 2,637,600.

5,4'-bipyridine-mono-1'-oxides with functional groups in the 2- and/or 3-position have not previously been synthesized, except with the exception of the 1'-oxide of 3-amino-5-(pyrid-4-yl)-pyrid-2-one (amrinone), and its 3-acetamido analogs. Moderately positive inotropic effects were claimed for the 1'-oxide of amrinone in German published patent application No. 3,045,637. The 1'-oxide of 3-cyano-6-methyl-5-(pyrid-4-yl)-1,2-dihydro-pyrid-2-one (milrinone) was mentioned as a metabolite of this active ingredient by A. A. Alousi, et al., New Drug Animal, Cardiovasc. Drugs 3, page 269 (1985). There was no report of possible heart stimulating activities of the latter compound.

DESCRIPTION OF THE INVENTION

The 3-cyano-5,4'-bipyridine-1'-oxides of the present invention are of the formula

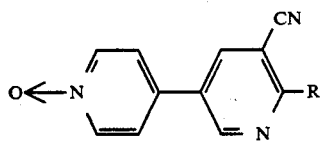
(I)

and their pharmaceutically acceptable acid addition salts,
wherein R is an amino, oxyalkoxy, or chloro residue.

As used throughout the specification and the claims, the term "amino" is intended to refer to unsubstituted and to substituted amino moieties. Accordingly, the term also includes alkyl substituted amino moieties, such as $C_{1-4}$ monoalkylamino, and $C_{1-4}$ dialkylamino residues, aminoalkylamino moieties, such as amino-$C_{1-4}$ alkylamino, di-($C_{1-4}$-alkyl)-amino-$C_{1-4}$-alkylamino, morpholino-$C_{1-4}$-alkylamino, piperazino, and $C_{1-4}$ alkyl, or hydroxy-$C_{1-4}$-alkyl substituted piperazino oxyalkylamino moieties, such as hydroxy $C_{2-4}$-alkylamino, di-(hydroxy-$C_{2-4}$ alkyl)-amino, $C_{1-4}$-alkoxy-$C_{2-4}$-alkylamino-, or morpholino residues; alkoxy moieties such as $C_{1-4}$ alkoxy residues, and oxyalkoxy moieties, such as hydroxy-$C_{2-4}$-alkoxy, or dihydroxy-$C_{3-4}$-alkoxy, or $C_{1-4}$-alkoxy-$C_{2-4}$-alkoxy residues.

Pursuant to the process of the present invention, compounds of formula (I) can be prepared by (a) converting an R-substituted-3-cyanobipyridine to its corresponding N-oxide, or (b) by substituting an R-residue or an R-unsubstituted precursor of the compound of formula (I). This can be suitably carried out by reacting (a) a 3-cyano-5,4'-bipyridine of the formula

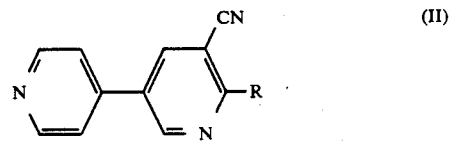
(II)

wherein R has the same meaning as given above, with a reagent suitable for producing pyridine-N-oxide, suitably with a peracid or with hydrogen peroxide, or (b) a 2-chloro-3-cyano-5,4'-bipyridine-1'-oxide of the formula

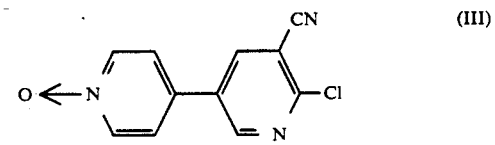
(III)

with a compound of the formula R-H, wherein R has the same meaning as given above, and, if required, converting the obtained compound of formula I with a pharmaceutically acceptable inorganic or organic acid into the corresponding acid addition salt.

When 3-cyano-6-methyl-5-(pyrid-4-yl)-1,2-dihydro-pyrid-2-one-1'-oxide was prepared by the direct N-oxidation of milrinone by peracetic acid, we found that the biological activity at the atrium of the guinea pig was drastically reduced, and we determined that this was the result of the N-oxidation at the pyrid-4-yl group.

With different animal models, a high vasodilatory and positive inotropic activity was found in vitro and in vivo for 3-cyano-2-morpholino-5,4'-bipyridine-1'-oxide. This is particularly surprising, since the 1'-oxide of milrinone, that was used for comparison, has only a very slight cardiotonic activity, although milrinone itself is one of the most effective nonglycosidic cardiotonic agents.

Suitably the (a) process variant is carried out in the presence of an inert organic solvent, such as glacial acetic acid or chloroform, at temperatures between from about 10° C. and about 100° C., suitably between from about 10° C. and about 60° C. Advantageously the reaction can be completed by further heating, such as at a temperature of from about 70° C. to about 100° C.

Peracids, which are suitable for carrying out the process variant (a), include peracetic acid, performic acid, perbenzoic acid, m-chloroperbenzoic acid, and perphthalic acid.

In a suitable embodiment of the process variant (b) the reaction is carried out in an inert organic solvent, such as a tertiary amine, pyridine, methyl glycol, dioxane, dimethylformamide, dimethyl sulfoxide, acetonitrile, or mixtures of these solvents or in an excess of the amine used.

If the process variant (b) is carried out in an inert organic solvent, the reaction can be suitably carried out in the presence of an acid acceptor such as KOH, NaOH, or $K_2CO_3$.

The cardiotonic and vasodilatory compounds of formula (I) can be used as the sole active ingredient in pharmaceutical preparations, in admixture with more than one compounds formula (I) or salt thereof, or in combination with other active ingredients, together with additional, pharmaceutically acceptable carriers and/or auxiliary substances that can be known per se, depending on the form of application or dosage.

The invention is exemplified in greater detail in the following examples.

EXAMPLE 1

3-Cyano-2-morpholino-5,4'-bipyridine-1'-oxide 1.1 g M-chloroperbenzoic acid is added at room temperature with stirring to a solution of 1.3 g 3-cyano-2-morpholino-5-(pyrid-4-yl)-pyridine in 20 ml chloroform. The reaction mixture is stirred for 48 hours at room temperature. Subsequently it is extracted with a bicarbonate solution and the chloroform phase is evaporated under vacuum. The residue is treated with water, filtered off with suction, dried at 110° C., and crystallized from a mixture of isopropanol and ethanol. Yield: 1.0 g (73% of the theoretical yield), with a melting point of 233° C.-235° C.

EXAMPLE 2

3-Cyano-2-morpholino-5,4'-bipyridine-1'-oxide

A mixture of 10 g 2-chloro-3-cyano-5,4'-bipyridine-1'-oxide and 40 ml morpholine is heated for 10 minutes at 70° C.-80° C. Subsequently, the mixture is evaporated to dryness under vacuum at an 80° C. bath temperature and the residue is collected, washed carefully with water and dried at 110° C. The product is refluxed for 1 hour with 150 ml dichloromethane, filtered off with suction, dried once again at 110° C. and crystallized from n-butyl acetate. Yield: 9.27 g (75% of the theoretical yield), with a melting point of 234° C.-236° C.

EXAMPLE 3

3-cyano-2-morpholino-5,4'-bipyridine-1'-oxide hydrochloride 1 g 3-Cyano-2-morpholino-5,4'-bipyridine-1'-oxide is dissolved in 5 ml 2N HCl and mixed under cooling with isopropanol and ether, filtered off with suction and dried at 100° C. Yield: 0.9 g (79.8% of the theoretical yield), with a melting point of 222° C.-223° C.

EXAMPLE 4

3-Cyano-2-(3-diethylamino-1-propylamino)-5,4'-bipyridine-1'-oxide

A mixture of 1 g 2-chloro-3-cyano-5,4'-bipyridine-1'-oxide and 1.35 g diethylamino-1-propylamine in 50 ml ethanol is refluxed for 4 hours. Subsequently, the mixture is concentrated under vacuum and the oil remaining behind is crystallized first from ethanol/diethyl ether and subsequently from methanol. Yield: 1.3 g (90.9% of the theoretical yield), with a melting point of 132° C.-133° C.

EXAMPLE 5

2-Chloro-3-cyano-5,4'-pyridine-1'-oxide

A mixture of 32.3 g 2-chloro-3-cyano-5-(pyrid-4-yl)-pyridine and 245 ml glacial acetic acid are heated on the water bath with stirring to 70° C., and 42 ml 40% peracetic acid is carefully added dropwise. A bright yellow, clear solution is formed.

After the addition, the temperature of the water bath is raised to 80° C. while continuing stirring. Subsequently, at intervals of 1 hour, a further 25 ml 40% peracetic acid are added dropwise to the mixture in portions of 5 ml each (5×5 ml). After 6 hours, the mixture is poured onto ice, the precipitate is filtered off with suction, washed intensively with water, then refluxed for 1 hour in 500 ml ethanol, filtered off with suction and dried. Yield: 33 g (95% of the theoretical yield), with a melting point of 261° C.-263° C.

EXAMPLE 6

3-Cyano-2-dimethylamino-5,4'-bipyridine-1'-oxide

2-Chloro-3-cyano-5,4'-bipyridine-1'-oxide and 3 g N,N-dimethylammonium-N,N-dimethyl carbamate is heated in 50 ml dimethylformamide for 2 hours on the boiling water bath and then allowed to cool. The crystalline precipitate, formed on standing overnight in the refrigerator, is filtered off with suction, crystallized from dimethylformamide and dried at 110° C. Yield: 2.9 g (93.2% of the theoretical yield), with a melting point of 282° C.-284° C.

EXAMPLE 7

3-Cyano-2-(2-hydroxy-ethylamino)-5,4-bipyridine-1'-oxide 5 g 2-Chloro-3-cyano-5,4'-bipyridine-1'-oxide and 8 ml ethanolamine are refluxed in 50 ml ethanol for 4 hours and then concentrated under vacuum. The residue is taken up in water, filtered off with suction, washed with water, dried at 110° C. and crystallized from ethanol/glacial acetic acid with addition of activated charcoal. Yield: 4.5 g (81.3% of the theoretical yield), with a melting point of 229° C.-231° C.

EXAMPLE 8

3-Cyano-2-(3-hydroxy-propylamino)-5,4'-bipyridine-1'-oxide hydrate

The procedure of Example 7 is followed to react and work up 5 g 2-chloro-3-cyano-5,4'-bipyridine-1'-oxide and 8 ml 3-amino-propan-1-ol. The product is recrystallized from ethanol/water. Yield: 4.87 g (78.4% of the theoretical yield), with a melting point of 141° C.-143° C.

EXAMPLE 9

3-Cyano-2-piperazino-5,4'-bipyridine-1'-oxide hydrochloride

A mixture of 2 g 2-chloro-3-cyano-5,4'-bipyridine-1'-oxide, 0.8 g piperazine, 0.52 g of $KHCO_3$ and 80 ml ethanol is refluxed for 3 hours and then evaporated to dryness under vacuum. The residue is dissolved in 10 ml 1N HCl and the solution is mixed with ethanol until crystallization occurs. After cooling overnight, the crystals that are formed are filtered off with suction and dried at 110° C. Yield: 2.23 g (81.2% of the theoretical yield), having a melting point of 255° C.-260° C.

EXAMPLE 10

3-Cyano-2-morpholino-5,4'-bipyridine-1'-oxide methane sulfonate 0.3 g 3-Cyano-2-morpholino-5,4'-bipyridine-1'-oxide is dissolved in acetone with heating. The solution is allowed to cool, then treated with 0.1 ml methanesulfonic acid and concentrated under vacuum in the rotary evaporator. The oily residue is dissolved in acetone. The resulting solution is mixed with ether until crystallization, then is cooled and filtered with suction. The material filtered out is washed with acetone and ether and dried. Yield: 0.3 g (74.0% of the theoretical yield), the melting point is 151° C.-154° C.

EXAMPLE 11

3-Cyano-2-(2,3-dihydroxy-propoxy)-5,4'-bipyridine-1'-oxide 300 mg Potassium hydroxide is dissolved in 15 ml glycerin with heating and 1 g 2-chloro-3-cyano-5,4'-bipyridine-1'-oxide is subsequently added. The reaction mixture is heated for 3 hours at 80° C.-90° C. with stirring, allowed to cool and treated with water. The precipitate obtained is filtered off with suction. Yield: 2 g (89.5% of the theoretical yield), having a melting point of 194° C.-196° C.

Isolated, Spontaneously Beating Atrium of the Guinea Pig

Experiments described by V. Hagen et al., in Pharmazie 44, 20 (1989) were carried out. The substituted 3-cyano-5,4'-bipyridine-1'-oxides showed a distinct and concentration-dependent inotropic effect.

For example, the compounds of Examples 1, 4 and 8 show a 30% increase in inotropy at concentrations of $2.9 \times 10^{-5}$, $4.3 \times 10^{-4}$ and $3.1 \times 10^{-4}$ moles/l. The low effects on the frequency are striking. The compound of Example 4 even shows a negative chronotropic effect, which can be regarded as particularly advantageous. By way of comparison, the positive inotropic effect of amrinone for an $ED_{30}$ is at $7.1 \times 10^{-4}$ moles/l.

The 1'-oxide of milrinone, in concentrations of $1.0 \times 10^{-5}$, $1.0 \times 10^{-4}$ and $1.0 \times 10^{-3}$ moles/l, shows an increase in inotropy of only 2.9%, 8.4% and 6.5% respectively.

Intravenous Administration to Anesthetized Dog

The tests were carried out as described by V. Hagen et al., in Pharmazie 44, 20 (1989).

A clear, dosage-dependent increase in the contraction force of the heart, as well as a significant lowering in the total peripheral resistance was observed under the influence of the substituted 3-cyano-5,4'-bipyridine-1'-oxides.

For example, the compounds of Examples 1 and 8 show a 50% increase in the contractility parameter $dp/dt_{max}$ at a dose of $1.56 \times 10^{-7}$ and $8.9 \times 10^{-6}$ moles/kg. The compound of Example 1 shows a 10% lowering of the diastolic blood pressure at a dose of $3 \times 10^{-6}$ moles/kg. On the other hand, the standard drug, amrinone, which was run for comparison, shows a positive inotropic effect with an $ED_{50}$ of $6.1 \times 10^{-6}$ moles/kg. For this model, the $ED_{50}$ of the compound 3-cyano-2-morpholino-5-(pyrid-4-yl)-pyridine is $1.6 \times 10^{-6}$ moles/kg At doses of $4.4 \times 10^{-7}$, $2.2 \times 10^{6}$ and $2.2 \times 10^{-5}$ moles/kg, the 1'-oxide of milrinone shows an increase in the contractility parameter $dp/dt_{max}$ of only 4%, 12% and 39% respectively.

Intravenous Administration to Anesthetized Minipig

The investigations were carried out on 6 male dwarf pigs (Mini-LEWE strain) with an average weight of 50 kg. The animals were thoractomized under artificial respiration with $N_2O$-$O_2$ (3:1) and muscle relaxation using d-tubocurarine. The blood pressure in the aorta ascendens was measured by means of a transducer and the pressure in the left ventricle (LVP) was measured with a tip manometer. The stroke volume was determined from the LVP signal by an integrator.

Using this model, some of the 2-substituted 3-cyano-5,4'-bipyridine-1'-oxides of formula I show a strong, dosage-dependent increase in the contractility of the heart ($dp/dt_{max}$), as well as a significant lowering in the total peripheral resistance in some cases. For example, for the compound of Example 1 at a dose of $2.8 \times 10^{-7}$ moles/kg, a 50% increase in the contractility parameter $dp/dt_{max}$ was found. On the other hand, under amrinone and milrinone, the contractility parameter, as measured on this model, increases as a function of the dose, but only insignificantly, up to a maximum value of 31.4% and 40.8% respectively at a dose of $8.5 \times 10^{-6}$ moles/kg.

We claim:

1. A 3-cyano-5,4'-bipyridine-1'-oxide of the formula (I)

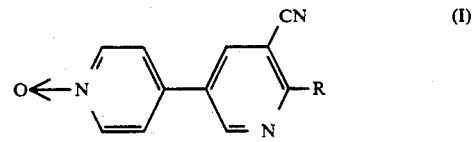

and its cardiotonically effective pharmaceutically acceptable acid addition salts,
wherein R is an amino, alkoxy, oxyalkoxy, or chloro radical.

2. The compound of claim 1, wherein the amino radical is an alkyl substituted amino, aminoalkylamino, or an oxyalkylamino radical, the alkoxy radical is $C_{1-4}$ alkoxy, and the oxyalkoxy radical is a $C_{1-4}$ oxaalkoxy radical.

3. The compound of claim 1, wherein the amino radical is a $C_{1-4}$-monoalkylamino, $C_{1-4}$-dialkylamino, amino-$C_{1-4}$-alkylamino, di-($C_{1-4}$-alkyl)-amino-$C_{1-4}$-alkylamino, morpholino-$C_{1-4}$-alkylamino, piperazino, piperazino substituted with a $C_{1-4}$-alkyl or with a hydroxy-$C_{1-4}$-alkyl radical, a hydroxy-$C_{2-4}$-alkylamino, di-(hydroxy-$C_{2-4}$-alkyl)-amino, $C_{1-4}$-alkoxy-$C_{2-4}$-alkylamino, or morpholino radical, the alkoxy radical is a hydroxy-$C_{2-4}$-alkoxy, dihydroxy-$C_{3-4}$-alkoxy, or a $C_{1-4}$-alkoxy-$C_{2-4}$-alkoxy radical.

4. The compound of claim 1, wherein the amino radical is a methylamino, ethylamino, dimethylamino, diethylamino, 2-hydroxyethylamino, 3-hydroxypropylamino, morpholino, or piperazino radical, and the alkoxy radical is a methoxy, ethoxy, 2,3-dihydroxypropoxy radical, or chloro radical.

5. A cardiotonic or vasodilator composition comprising a cardiontonically and/or vasodilatingly effective amount of a compound of formula (I) of claim 1, and a pharmaceutically acceptable carrier.

6. A method for imparting a heart stimulating cardiotonic effect or vasodilation to a patient in need therefor, which comprises administering to the patient the pharmaceutical preparation of claim 5.

* * * * *